United States Patent [19]
Zavislan et al.

[11] Patent Number: 5,632,741
[45] Date of Patent: May 27, 1997

[54] EPILATION SYSTEM

[75] Inventors: James M. Zavislan, Pittsford, N.Y.; Steven H. Tomson, deceased, late of Cape Elizabeth, Me., by Ramey Tomson, Executrix

[73] Assignee: Lucid Technologies, Inc., Henrietta, N.Y.

[21] Appl. No.: 376,205

[22] Filed: Jan. 20, 1995

[51] Int. Cl.$^6$ .............................. A61N 5/06; A61B 17/00
[52] U.S. Cl. .............................................................. 606/9
[58] Field of Search ........................... 606/9, 10, 11, 606/12, 15, 16; 607/88, 89

[56] References Cited

U.S. PATENT DOCUMENTS

| | | |
|---|---|---|
| 2,590,791 | 6/1952 | LeBouck . |
| 3,538,919 | 11/1970 | Meyer . |
| 3,693,623 | 9/1972 | Harte . |
| 3,834,391 | 9/1974 | Block . |
| 4,388,924 | 6/1983 | Weissman . |
| 4,608,978 | 9/1986 | Rohr . |
| 4,617,926 | 10/1986 | Sutton ................................ 606/9 |
| 5,059,192 | 10/1991 | Zaisus . |
| 5,226,907 | 7/1993 | Tankovich . |
| 5,397,327 | 3/1995 | Koop et al. ......................... 606/17 |

OTHER PUBLICATIONS

Gilchrest et al "Chilling Port Wine Stains Improves the Response to Argon Laser Therapy", Plastic and Reconstructive Surgery Feb. 82 vol. 69 No. 2. pp. 278–283.

Illustrated Cutaneous Laser Surgery—A Practitioner's Guide, by Jeffrey S. Dover, et al, published by Appleton & Lange, Division of Prentice Hall, 1990, pp. 14–18.

Clinical Photomedicine, a text edited by H. W. Lim, et al, published by Marceldekker, Inc., 1993, pp. 25, 28–31.

Operator Manual for "Ultrapulse" 5000 and 5000L Carbon Dioxide Surgical Lasers, published by Coherent, Coherent, Inc., 1992 pp. 4–33 and 34.

Cosmetic and Medical Electrolysis and Temporary Hair Removal by R. N. Richards, et al., published by Medric Ltd., 1991, pp. 22–26.

Primary Examiner—Angela D. Sykes
Assistant Examiner—Sonya Harris-Ogugua
Attorney, Agent, or Firm—M. Lukacher; K. Lukacher

[57] ABSTRACT

In order to permanently remove hair growing in subcutaneous (below the skin's surface) tissue and to do so permanently, the hair and its root structure is epilated (vaporized) in an ablation cavity of essentially the same size and shape as the volume occupied by the root structure which includes follicle, the follicle bulb and the dermal papilla. Optical energy is used which is of a wavelength and fluence sufficient to cause epilation in the cavity without relying upon selective photothermolysis thereby limiting damage to tissue outside of the hair root structure. To find and restrict the optical energy to the epilation cavity, an optical system, which may be constituted of a single lens, having a numerical aperture of F/5–5.8 is used. The beam is generated by a laser which may be operated in a pulse mode and contained in a hand piece having the optical system at the end thereof. In order to facilitate epilation, a medium such as a cold compress or a freezing agent, may be applied before application of the laser energy in order to cause the root structure and the hair to move to a location generally perpendicular to the surface of the skin. During application of the laser energy, the root structure and the hair, if present, is progressively ablated and vaporized until the bottom of the hair bulb is reached at which time the beam is turned off. Because of the shaping effect of the optical system, the beam is diffused so as to have insufficient fluence to damage the tissue below the bottom of the hair follicle bulb.

23 Claims, 6 Drawing Sheets

EPILATION SYSTEM

BACKGROUND OF THE INVENTION

The present invention relates to systems for epilation or the permanent removal of hair from subcutaneous tissue (tissue at and below the skin), and particularly to an improved system (method and apparatus) for epilation utilizing laser beam energy.

This application is related to an earlier, commonly owned, application, U.S. Ser. No. 08/094,296 filed Jul. 21, 1993 pending and entitled, Dermatological Laser Treatment System With Electronic Visualization of the Area Being Treated. The present invention provides a treatment system wherein the treatment is epilation and the laser energy is shaped into a beam which matches the geometry of the hair root (the hair and the hair follicle including the bulb and dermal papilla at the base thereof). This beam is of sufficient fluence at the selected wavelength to progressively ablate or vaporize the hair root, but because of its shape and the divergence at depth below the hair root, only the hair root is treated. The beam may be shaped to have its narrowest cross-section or waist at the skin's surface and a divergence which decreases the optical energy density outside of an ablation cavity which includes essentially only the hair root.

Optical beams for hair removal have been suggested in several patents which are discussed below. The optical energy is not used to ablate the hair and its root structure as provided for by the present invention, in that beam delivery system is not an optical system which shapes and restricts the beam to a subcutaneous ablation cavity, that is a volume where ablation can occur and is restricted.

In U.S. Pat. No. 5,059,192, issued to Zaias on Oct. 22, 1991 and in Weissman, et al., U.S. Pat. No. 4,388,924 issued Jun. 21, 1983 and in a patent issued Jul. 13, 1993 to Tankovich, U.S. Pat. No. 5,226,907, reliance is placed on selective photothermolysis, that is the selective absorption of the incident laser radiation by the melanin in the follicle to cause localized heating.

Sutton, in U.S. Pat. No. 4,617,926 issued Oct. 21, 1986, alleges that the hair can be used as a optical waveguide to conduct the optical energy to the base of the follicle without damaging the surrounding tissues. No explanation is given as to how hair, which is not transparent nor hollow, can function as a waveguide, so that the operability of the Sutton proposal is questionable. Other proposals have involved probes which must be inserted much like electrolysis needles to deliver the optical energy directly to the hair root. See Block U.S. Pat. No. 3,834,391 issued Sep. 10, 1974 and Mayer, U.S. Pat. No. 3,538,919 issued Nov. 10, 1970.

The delivery of the energy may be through the use of a hand piece having means for scanning a beam in order to locate the entrance to the hair root structure at the skin. Other automatic and semiautomatic systems for locating a housing carrying the laser beam and its optical system may be used. The U.S. patent to Weissman referenced above shows one such system. Another system is described in French Patent Application 2,590,791 published Jun. 5, 1987.

Accordingly, it is the principal object of the present invention to provide an improved epilation system for permanent removal of hair which relies upon geometric shaping of a laser beam so as to ablate only the hair and the root structure and vascular system which supports the growth of the hair, without reliance on selective photothermolysis, but rather on the geometry of the beam in order to limit the tissue which is surgically removed thereby reducing damage to surrounding tissue.

It is a still further object of the present invention to provide an improved epilation system using optical means for beam shaping and relying upon the spatial characteristics of the beam (Gaussian/Truncated) and the divergence of the beam due diffraction effects in order to adjust the geometry of the beam and to confine it to an ablation cavity containing and limited to the root structure to be excised by the laser beam.

Briefly described, the invention utilizes means for directing a laser beam of sufficient fluence at the selected wave length to vaporize a hair and its root structure which surrounds and supports the growth of the hair in the epidermis, dermis and subcutaneous tissue of the skin. The beam is directed in a manner to optically confine it to the root structure within an ablation cavity, spatially matching the root structure. Laser energy is, thereby, delivered from the beam to expose the hair and the root structure progressively inwardly of the skin's surface until the root structure and any hair therein is ablated without substantial damage to tissue surrounding the root structure.

BRIEF DESCRIPTION OF THE DRAWINGS

The foregoing and other features and advantages of the invention will become more apparent from a reading of the following description in connection with the accompanying drawings in which.

DETAILED DESCRIPTION OF THE PREFERRED EMBODIMENT

The following description refers to the foregoing drawings.

Figure 1:
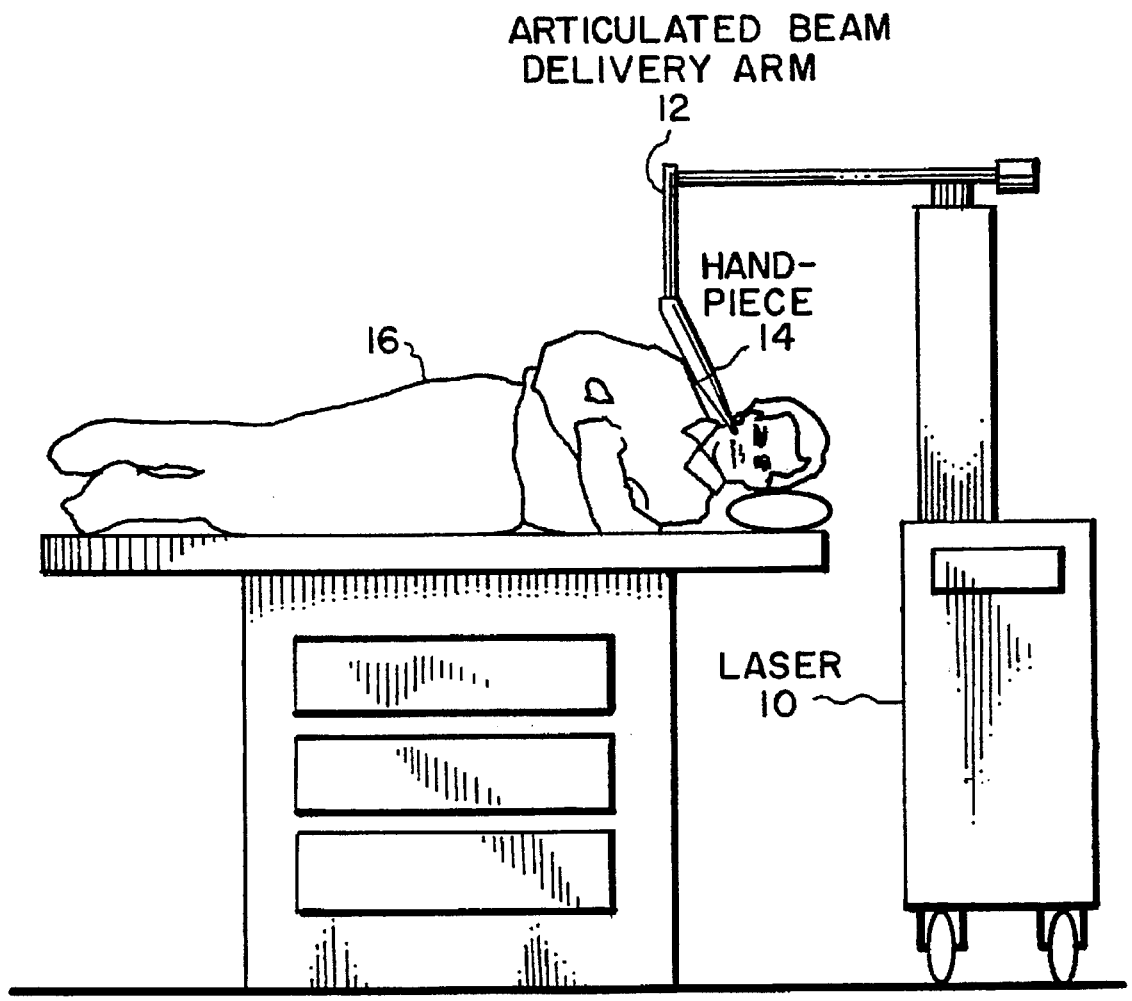
FIG. 1 is a diagram schematically showing apparatus in accordance with, and the method of practicing, the invention.

As shown in FIG. 1 a laser generator 10 provides a laser beam. The laser beam is delivered to the patient 16 through an articulated arm 12 to a laser focusing handpiece 14.

Figure 2:
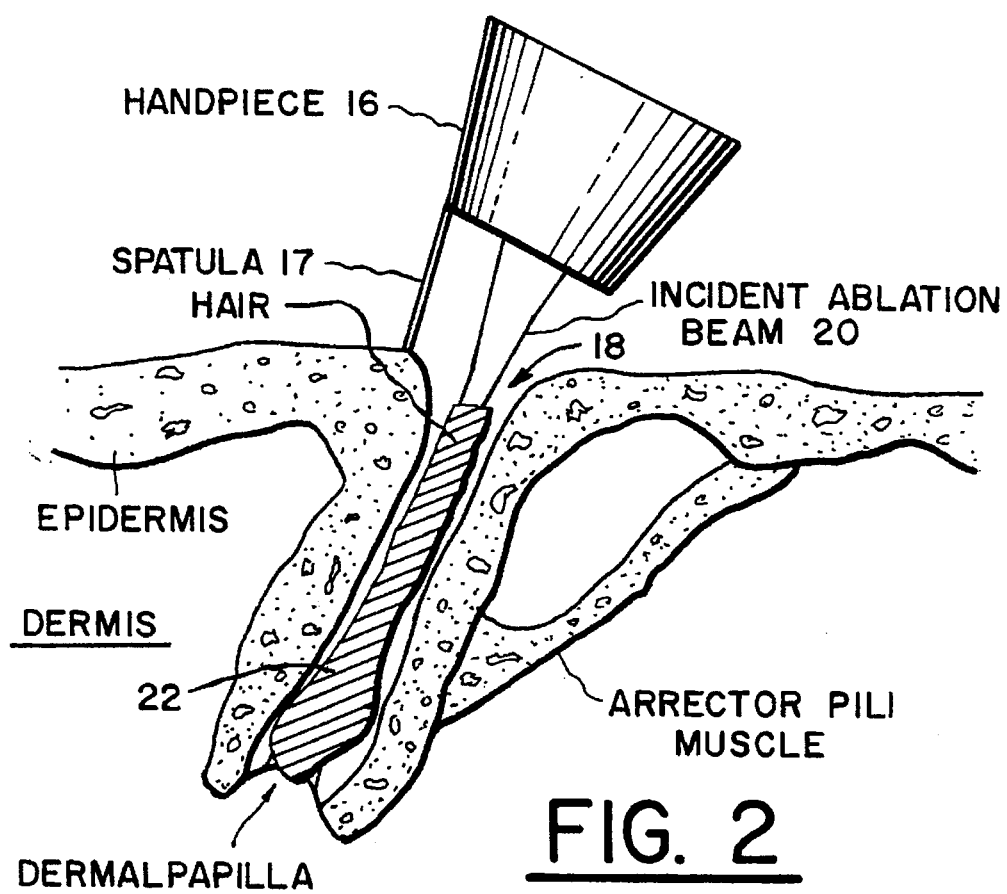
FIGS. 2 and 3 are cross-sectional views through an individual hair identifying the anatomy thereof and showing the optical system for directing a laser beam into an ablation cavity where the root structure and any hair therein is progressively vaporized.
Figure 3:
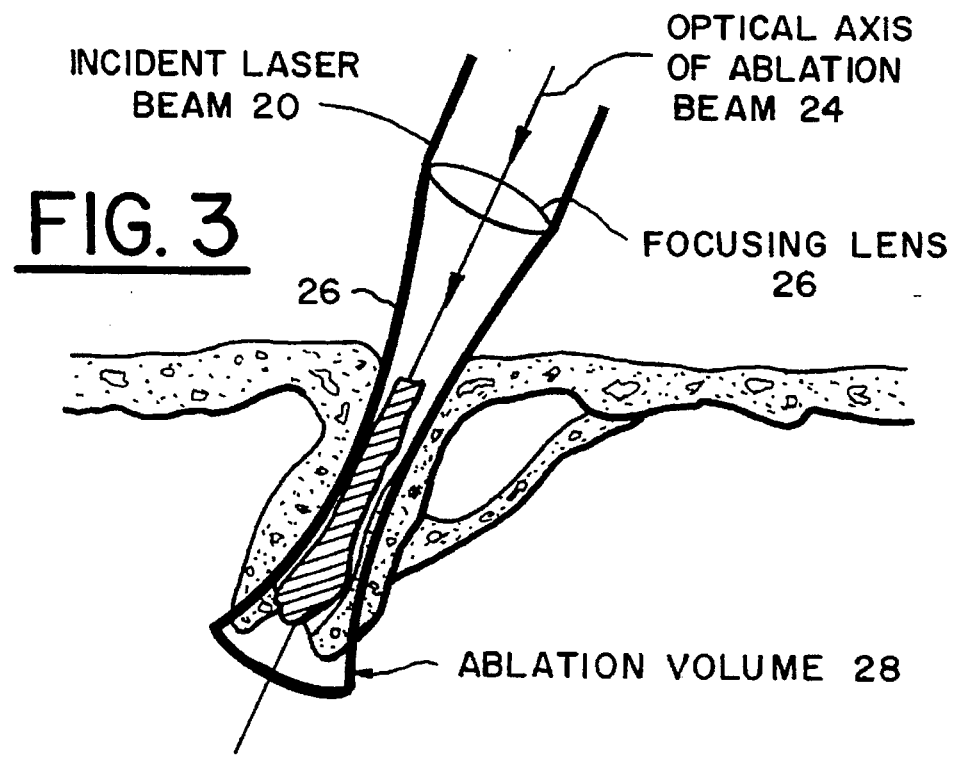
Figure 4A:
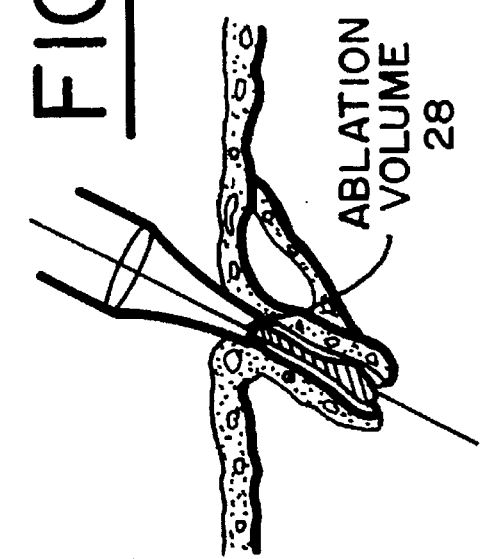
FIGS. 4a–d are cross-sectional views similar to FIG. 3, but showing how a volume is cored or surgically excised by the beam after the laser energy has been applied.
Figure 4B:
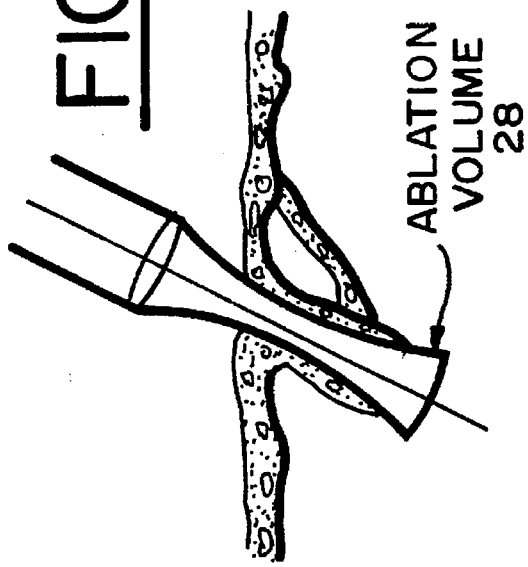
Figure 4C:
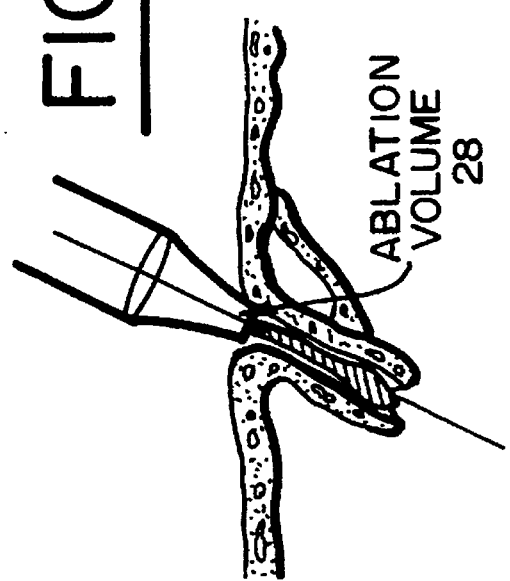
Figure 4D:
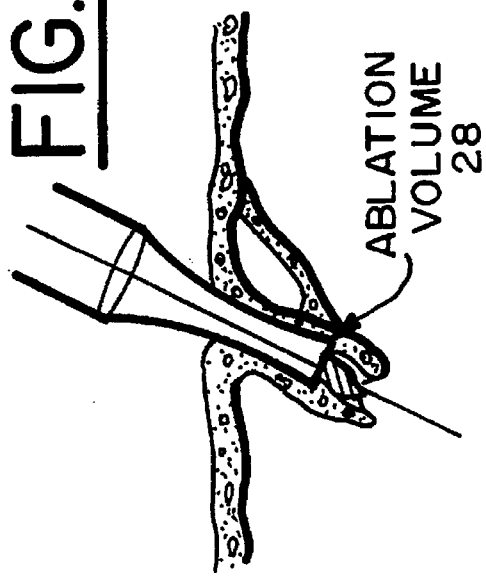

FIG. 2 shows a cross-section of the distal end 16 of the handpiece and the relevant structures in the skin. The incident ablation beam 20 is directed to the opening 18 of the hair follicle 22. The optical axis 24 of the ablation beam is oriented parallel to the hair follicle as shown in FIG. 3. The margins 26 of the beam are shown. These margins 26 may be considered to be the full width half maximum or the $(1/e)^2$ intensity contours. These margins 26 are created by the focusing and diffraction parameters of the incident ablation beam. These margins define the sidewalls of the ablation cavity or volume 28. The optical system controls the beam parameters to keep the contour (the margins 26) matched to the overall shape of the follicle without moving the handpiece containing the optical system during epilation. Thus, the beam is nominally constant diameter until reaching the base of the hair follicle where its diameter begins to grow due to the predetermined diffractive spread. The bottom of the volume is defined by the length of time the laser beam is applied to the follicle. FIGS. 4a–4d show a series of cross-sections of the follicle versus exposure time. FIG. 4a shows the cross-section as the beam is first applied. With increased exposure time more of the hair and follicle are removed. The ablation volume 28 grows with time in each of the "snap-shot" views, which are progressively later in time after initiation of the beam.

The margins 26 of the beam are defined by the optical system. The diameter at the opening of the ablation cavity on volume 28 is proportional to the laser beam size at the skin surface. The shape of the ablation cavity 28 depends on the location of the beam waist relative to the skin, the optical parameter of the transport and focusing optics, and the mode distribution of the laser source. The light distribution as a function distance from the beam waist follows well known Gaussian beam optics. The range from the waist along the beam axis, which defines the ablation volume, may be the Rayleigh range of the beam. See for example A. Yariv, *Quantum Electronics*, 2nd ed. (Wiley, New York, 1975) pages 99–127.

For efficient ablation of hair and its surrounding follicle, the beam should provide a small physical opening at the surface and then gradually diverge in order to engulf the entire hair bulb and papilla at the base of the follicle. Thus, the ablation beam and cavity will match the geometry of the hair and hair follicle. The hair and hair follicle is narrow at the surface and gradually becomes a larger diameter at the base of the hair bulb. One method for achieving this result with 10.6 µm laser radiation is to use a F/5.8 focusing optical system and then position the beam waist at the skin surface. The beam waist diameter at the focusing lens is 3.25 mm. This beam provides approximately 0.06 mm diameter hole at the skin surface. The diameter of the cavity increases with increasing depth. At 3.0 mm in depth the diameter of the cavity is approximately 0.4 mm. Below is a table of the $(1/e)^2$ diameter of this optical configuration.

| Depth Below Surface (mm) | $(1/e)^2$ Diameter (mm) |
|---|---|
| 0 | 0.061 |
| 0.5 | 0.09 |
| 1 | 0.145 |
| 1.5 | 0.207 |
| 2 | 0.27 |
| 2.5 | 0.335 |
| 3.0 | 0.4 |

This configuration reduces the diameter of the orifice in the epidermis while increasing the volume of the follicle tissue removed below the epidermis without repositioning the beam. Faster F/# beams are possible but produce larger divergence which decrease the energy density at greater depths. This will increase the number of pulses required to remove the hair follicle.

The preferred embodiment of the invention uses a pulsed $CO_2$ laser (10—FIG. 1) such as a Coherent ULTRAPULSE (3270 West Bayshore Road, Palo Alto, Calif.). The absorbed radiation is converted into heat. Tissue destruction occurs wherever the tissue temperature exceeds 50°–60° C. Heating above 100° C. vaporizes the tissue. The laser is operated in a short pulse length mode. The short pulse duration is chosen to be much less than the thermal diffusion time of the absorbing tissue. Diffusion times are approximately 1 µm/µsec (Jeffry S. Dover, Illustrated Cutaneous Surgery, Appleton & Lange, Norwalk (1990), page 15). At sufficient optical fluences >2 to 3 Joules/cm$^2$ the short pulses produce large thermal gradients in the tissue which result in tissue ablation: the vaporization of tissue without thermal destruction of the adjacent tissue.

The preferred energy range for a Ultrapulse $CO_2$ laser is 25 mJ–250 mJ per pulse. 25 mJ per pulse at 2 Watts average power concentrated to a 0.2 mm spot size gives cosmetically acceptable results when treating hair follicles on the chin of a fair skinned individual. At 25 mJ energy per pulse, there is no bleeding in the ablated cavity and no apparent tissue charring.

The exact energy delivered per pulse will depend on the location of the hair follicle and the patient's skin. However, the spot size and the energy per pulse are the most important parameters in tissue ablation when using a highly absorbed wavelength. The average power, i.e. the number of pulses per second, determines to first-order only the ablation rate. This relationship remains approximately correct until the pulses are spaced closer than the thermal diffusion time of a volume of tissue. The volume of tissue is defined by the area of illumination times the absorption depth of the illuminating wavelength. The distance of the handpiece 16 from the skin may be set by a spacer or spatula 17 (FIG. 2).

Other wavelengths can be used holmium: yttrium-aluminum garnet ($\lambda$=2.12 µm) lasers and erbium: yttrium-aluminum garnet ($\lambda$=2.94 µm) lasers can be used. These lasers offer similar ablation properties as $CO_2$ lasers.

Another embodiment uses focussed uniform or nearly uniform beams (non-uniformity <10%). In this embodiment, the diffraction properties taught by Forbes (G. W. Forbes, "Scaling properties in the diffraction of focussed waves and an application to scanning beams," American Journal of Physics, Vol. 62, No. 5, May 1994, pages 434–443) are used to define a beam pattern that maintains a uniform beam width for a predetermined length and then diverges. This provides a beam pattern that matches the follicle and also provides a mechanism that greatly slows the ablation rate at a predetermined depth. The optical system of the various embodiments may be contained in the handpiece 14 and desirably at the end 16 thereof.

Figure 6:
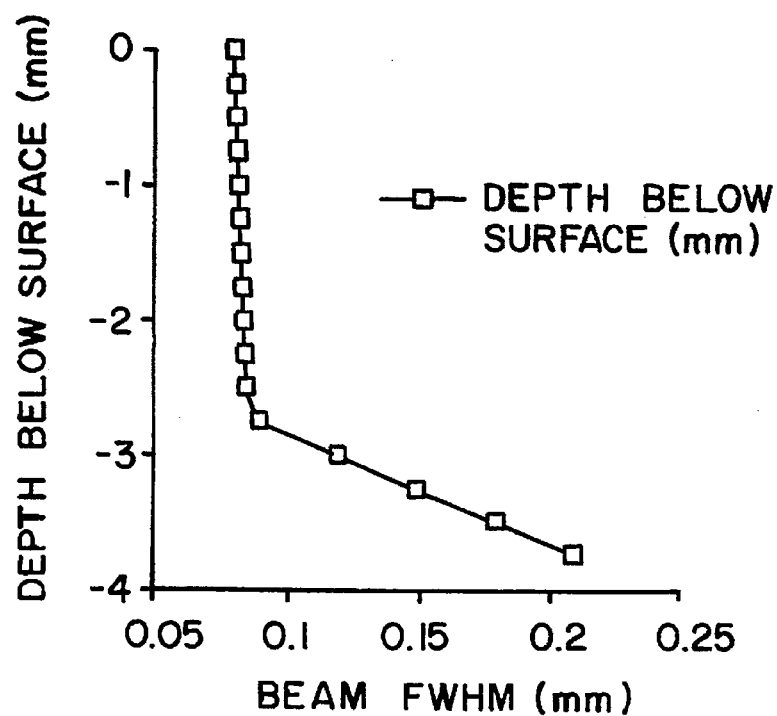
FIGS. 6 and 7 are plots showing beam shape (diameter at full width half maximum intensity (FWHM)) and relative beam fluence, respectively, with respect to depth below the surface.
Figure 7:
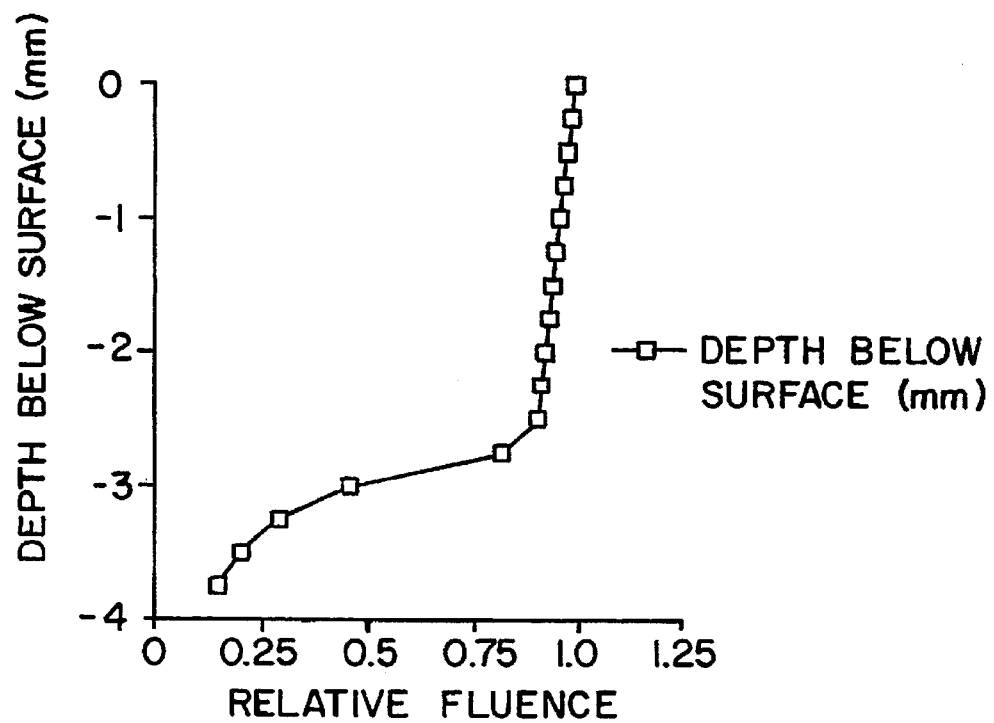
Figure 8:
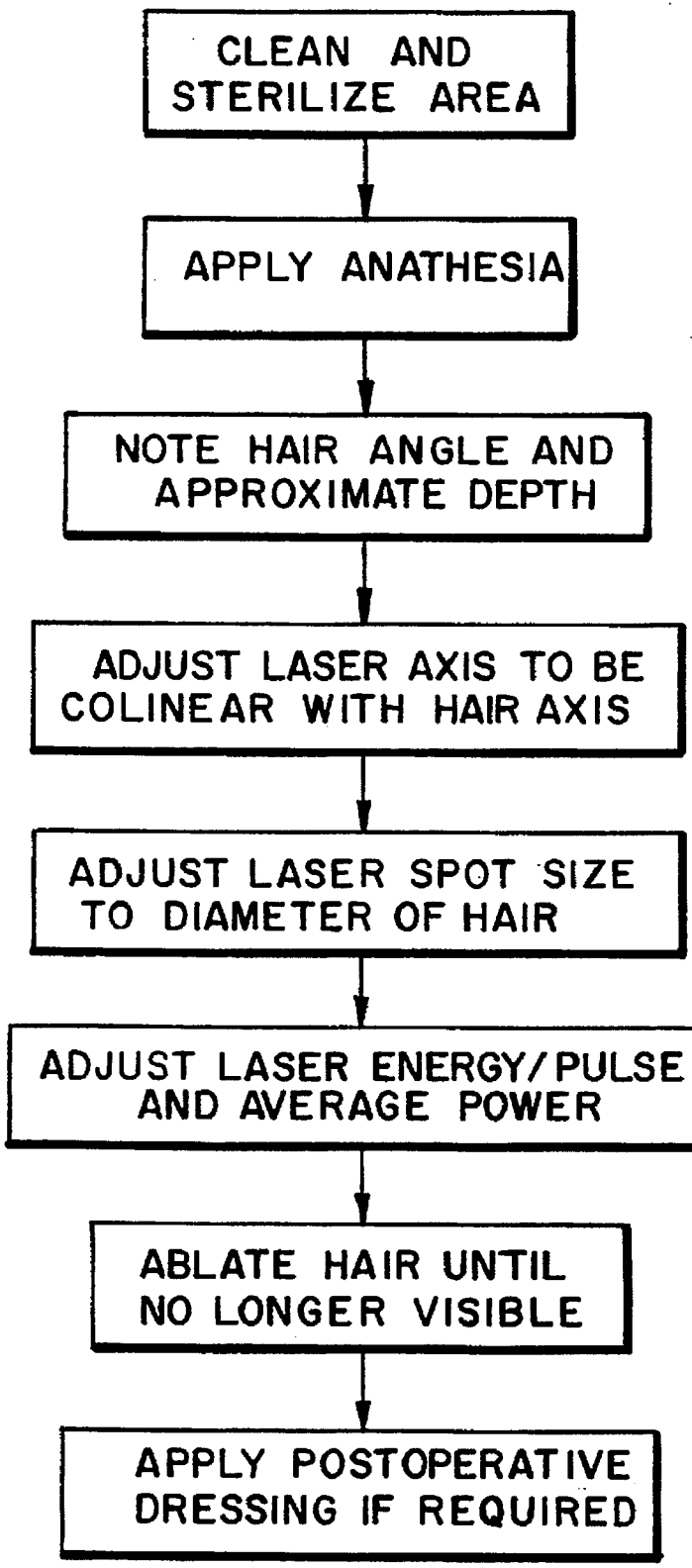
FIG. 8 is a flowchart showing the steps in the method of ablative epilation which is carried out in accordance with the invention.

In this embodiment, the incident laser beam is expanded and apertured to provide a nearly uniform beam at the lens aperture. This beam is then focussed by the lens and directed to the skin surface. The focal length of the lens is 51 mm; the aperture diameter is 6.35 mm, and the wavelength is 10.6 µm. The full width half maximum diameter of the beam is shown in FIG. 6. The y-axis is the distance from the geometrical focus of the lens which is at the surface of the skin, and thus FIG. 6 represents the diameter of the ablation volume versus depth. FIG. 7 shows the relative fluence as function of depth below the skin. The fluence decreases quickly below 3.5 mm. Thus, this beam shape is well suited to remove a follicle 3 mm below the surface but quickly reduce the ablation rate below 3.5 mm. The length of this region can be adjusted by adjusting the focal length of the lens and the beam size at the lens (as taught by Forbes).

In another embodiment, the average power of the laser is adjusted during the ablation to control the depth of the ablation. Also, the beam parameters are changed from ultra-pulse to slow pulse at the end of ablation to cause a small charred plug to form at the bottom of the ablation volume to aid in healing and prevent postoperative infection.

Figure 5:
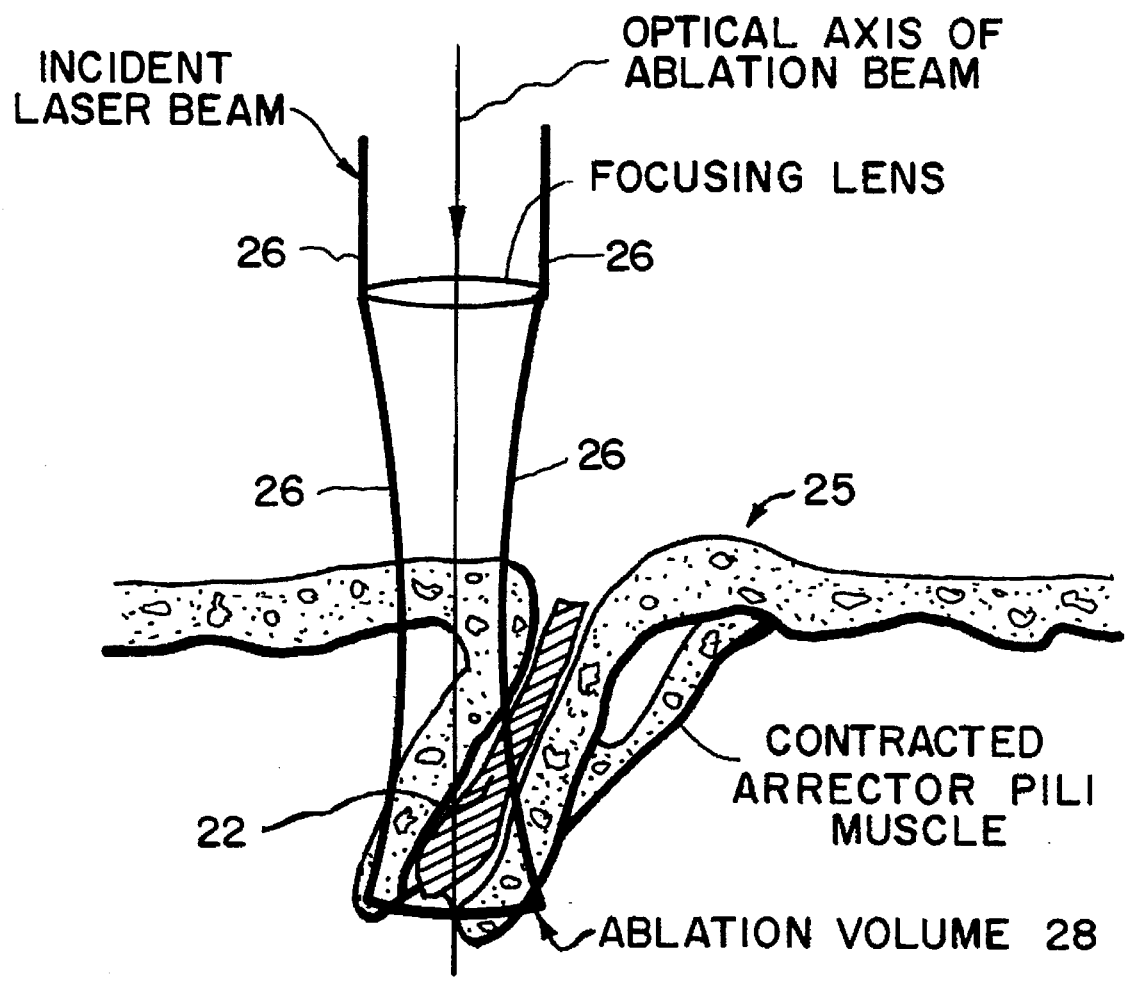
FIG. 5 is a view similar to FIG. 3, but after an agent is applied to the skin in the vicinity of the hair in order to turn the hair and the follicle to a position more perpendicular to the surface of the skin than is the case without such treatment.

FIG. 5 shows the skin 25 and follicle 22 after a topical, intradermal or subcutaneous anesthetic solution is applied. A sympathomimetic drug such as epinephrine may be contained in the solution. This drug causes the arrector pili muscles which are attached to the base of the follicle to constrict. Alternatively or in addition, a cold compress may be used. This action forces the hair follicle to assume an orientation closer to perpendicular to the skin surface and the beam axis may be similarly oriented. The laser enters the skin at a distance equal to the distance between the epidermal bulge and the hair opening, but on the opposite side of the hair opening.

From the foregoing description it will be apparent that an improved epilation system has been provided. Variation and modifications of the apparatus and method of the herein described system will undoubtedly suggest themselves to those skilled in the act and will be within the scope of the invention. Thus the foregoing description should be taken as illustrative rather than in a limiting sense.

It is claimed:

1. The method of epilation of hair in skin having an epidermis, dermis and subcutaneous tissue which comprises the steps of generating a laser beam of such wavelength and sufficient fluence to vaporize a hair and root structure of the hair which surrounds and supports the growth of the hair in the epidermis, dermis and subcutaneous tissue of the skin, optically confining said beam to substantially only said root structure by filling an ablation cavity spatially matching said root structure with said beam, thereby delivering laser energy from said beam to expose said hair and root structure progressively inwardly of said skin's surface until said root structure and the hair therein is epilated without substantial damage to tissue surrounding said root structure and without moving said beam.

2. The method according to claim 1 wherein said optically confining step is carried out with the aid of optics which restricts divergence of said beam to maintain said beam in said ablation cavity without moving said optics.

3. The method according to claim 2 wherein said generating step is carried out to provide said beam with a shape about an axis extending centrally through said ablation cavity via an entrance thereto, and said confining step is carried out with said optics to form a waist of said beam which diverges from said entrance over a range along said axis to include a volume generally equal to the volume of a hair follicle bulb of said root structure including dermal papilla and vascular system thereof thereby coring said bulb by ablation out of the skin.

4. The method according to claim 3 wherein said confining step is carried out to provide said beam with about equal fluence across a cross-section of said beam at said entrance where said beam is entering the cavity.

5. The method according to claim 3 wherein said confining step is carried out to provide said beam with a Gaussian irradiance distribution and with a cross-section of said beam perpendicular to said axis and with said range being the Rayleigh range of said beam from a waist which is a narrowest cross-section of said beam which is located at the entrance of said cavity.

6. The method according to claim 3 wherein said confining step is carried out so that the waist of said beam is a narrowest cross-sectional area thereof and is located at the surface of said skin which is the location of the entrance of said ablation cavity.

7. The method according to claim 5, wherein said confining step is carried out so that said waist is located at the surface of said skin which is the location of the entrance of said ablation cavity and said optics is located above the surface of said skin.

8. The method according to claim 1 wherein said confining step is carried out using an optical system having a numerical aperture from about F 5 to F 5.8.

9. The method according to claim 2 wherein said optics is a lens having a numerical aperture of about F 5 to F 5.8.

10. The method according to claim 3 wherein said generating step is carried out to generate said laser beam at a wavelength at which said hair and said hair root structure are non-selectively thermalyzed sufficiently to ablate tissue in said cavity progressively.

11. The method according to claim 10 wherein said wavelength is at least 1.3 micrometers.

12. The method according to claim 10 wherein said generating step is carried out in pulses of sufficient energy per pulse and at a sufficient repetition rate to progressively ablate the tissue in said cavity.

13. The method according to claim 1 further comprising the step of orienting said beam so that an axis of said beam is approximately coaxial and concentric with said hair.

14. The method according to claim 1 further comprising the step of directing said beam along a path approximately perpendicular to the skins surface in the vicinity of the hair which path intersects the hair follicle bulb's dermal papilla.

15. The method according to claim 1 further comprising the step of causing skin to bulge in the vicinity of the hair with the agency of a cold compress or topical synpatominetic solution thereby orienting the hair and the hair root structure in the direction generally perpendicular to the surface of said skin, and orienting said beam along said perpendicular direction in alignment with the hair or spaced from said bulge in the direction of said hair such that the path of said beam intersects the hair follicle bulb of the root structure in the vicinity of the dermal papilla thereof.

16. The method according to claim 2 wherein said optics is selected from the group consisting of Gaussian beam optic and diffractive optics.

17. Apparatus for epilation which comprises means for generating a laser beam of wavelength and sufficient fluence to vaporize a hair and its root structure which surrounds and supports the growth of the hair in the epidermis, dermis and subcutaneous tissue of the skin, means for optically confining said beam to substantially only said root structure to fill an ablation cavity spatially matching said root structure, and means for delivering laser energy from said beam to expose said hair and root structure progressively inwardly of said skins surface until said root structure and any hair therein is epilated without substantial damage to tissue surrounding said root structure and without movement of said beam.

18. The apparatus according to claim 17 wherein said optical confining means comprises optics means for restricting divergence of said beam to maintain said beam in said ablation cavity.

19. The apparatus according to claim 18 wherein said optics means is selected from the group consisting of Gaussian beam optics and diffractive optics.

20. The apparatus according to claim 19 wherein said optics means is an optical system having a numerical aperture from about F 5 to F 5.8.

21. The apparatus according to claim 17 wherein said generating means includes means for generating said laser beam at a wavelength at which said hair and said hair root structure are non-selectively thermalyzed sufficiently to ablate tissue in said cavity progressively.

22. The apparatus according to claim 21 wherein said wavelength is at least 1.3 micrometers.

23. The apparatus according to claim 17 wherein said generating means includes means for generating said beam in pulses of sufficient energy per pulse and at a sufficient repetition rate to progressively ablate the tissue in said cavity.

* * * * *